US006469044B1

(12) United States Patent
Zisapel

(10) Patent No.: US 6,469,044 B1
(45) Date of Patent: Oct. 22, 2002

(54) METHOD FOR TREATING PATIENTS SUFFERING FROM DRUG DEPENDENCIES WHICH LEAD TO PLASMA MELATIONIN DEFICIENCIES

(75) Inventor: Nava Zisapel, Tel Aviv (IL)

(73) Assignee: Neurim Pharmaceuticals (1991) Ltd., Tel Aviv (IL)

( * ) Notice: Subject to any disclaimer, the term of this patent is extended or adjusted under 35 U.S.C. 154(b) by 0 days.

(21) Appl. No.: 08/381,535

(22) Filed: Feb. 1, 1995

(51) Int. Cl.[7] .................. A61K 31/405; A61K 31/40
(52) U.S. Cl. .................. 514/415; 514/412; 514/414; 514/419
(58) Field of Search ................. 514/412, 414, 514/415, 419

(56) References Cited

U.S. PATENT DOCUMENTS

| | | | |
|---|---|---|---|
| 4,600,723 A | 7/1986 | Short et al. | 514/416 |
| 4,800,087 A | 1/1989 | Mehta | 424/497 |
| 4,882,137 A | 11/1989 | Staples et al. | 424/423 |
| 5,242,941 A | 9/1993 | Lewy et al. | 514/416 |
| 5,430,029 A * | 7/1995 | Biella et al. | 514/220 |

FOREIGN PATENT DOCUMENTS

| | | |
|---|---|---|
| EP | 513702 | 11/1992 |
| WO | 9407487 | 4/1994 |

OTHER PUBLICATIONS

Guardiola–Lemaitre et al., *Pharmacology Biochemistry and Behavior*, 41, pp. 405–408 (1992).
Dawson et al., *J. Of Pineal Research*, 15, pp. 1–12 (1993).
Hitoshi et al., Chemical Abstracts, vol. 121, No. 11, Sep. 12, 1994.

"Polifarma's Sleep Normaliser", Dialog File Supplier: PHIND, Mar. 13, 1992.

Van Coevorden, Anne et al., "Neuroendocrine rhythms and sleep in aging men", in Endocrine Rhythms in Senescence, E651–661, American Physiological Society, 1991.

Aldhous, M. et al., "Plasma concentrations of melatonin in man following oral absorption of different preparations," *Br. J. Clin. Pharmac.*, vol. 19, pp. 517–521, 1985.

Brown, Gregory M., "Melatonin in Psychiatric and Sleep Disorders," *Pharamacology and Pathophysiology, CNS Drugs*, vol. 3 pp. 209–226, 1995.

Ardent, Josephine et al., "Light and melatonin as zeitgebers in man," *Chronobiology International*, , vol. 4, No. 2, pp. 273–282, 1987.

Ardent, J., "Melatonin," *Clinical Endocrinology*, vol. 29, pp. 205–229, 1988.

Jimerson, David C., "Urinary Melatonin Rhythms During Sleep Deprivation in Depressed Patients and Normals" *Life Sciences*, vol. 20, pp. 1501–1508, 1977.

* cited by examiner

Primary Examiner—Theodore J. Criares
(74) *Attorney, Agent, or Firm*—Rothwell, Figg, Ernst, & Manbeck

(57) ABSTRACT

A method of treating a patient suffering from a dependence on, tolerance of, or addiction to at least one benzodiazepine comprises administering melatonin to said patient on a daily basis in an amount sufficient to treat said dependence on, tolerance of, or addiction to said benzodiazepine.

14 Claims, 1 Drawing Sheet

METHOD FOR TREATING PATIENTS SUFFERING FROM DRUG DEPENDENCIES WHICH LEAD TO PLASMA MELATONIN DEFICIENCIES

FIELD OF THE INVENTION

The present invention relates to a method for treating a patient who is suffering from a dependence on, tolerance of, or addiction to at least one benzodiazepine or is at risk of becoming dependent upon, tolerant of, or addicted to such a drug. More specifically, the invention relates to such a method which comprises administering an amount of melatonin effective to treat or prevent the dependence, tolerance or addiction.

BACKGROUND OF THE INVENTION

Insomnia is a frequently encountered problem in modern society: it is estimated that almost one third of the U.S. population suffers from this condition to some extent. The problem is particularly troublesome among the elderly. Benzodiazepine hypnotics are among the most commonly used drugs in the therapeutic treatment of insomnia. Although the precise mechanism of action of these drugs on sleep induction has not been completely elucidated, it is assumed that they exert their activity through a benzodiazepine/GABA-A (gamma amino butyric acid) receptor complex. As insomnia is thought to be associated with derangement of the normal sleep-wake cycle, it is possible that the effects of these drugs on sleep induction may be accomplished by phase-shifting the internal biological clock in the brain.

Indiscriminate and/or prolonged use of benzodiazepine hypnotics often results in the development of tolerance to the drugs, and rebound or withdrawal phenomena can appear following abrupt cessation of the drugs. The extent of these phenomena depends upon both the compound and its dosage.

Dependence upon benzodiazepines also often develops in persons seeking to overcome an addiction to a hallucinogenic drug who take one or more benzodiazepines to ease their anxiety and convulsions during withdrawal from the narcotic(s) to which they are addicted.

In the 1990 U.S. National Household Survey of the Use of Psychotherapeutic Medications, about 8% of the medical users of hypnotics advanced a prescribed dose on their own, an increase of 25 over those who responded similarly in a 1979 survey. Inasmuch as the survey found that 2.6% of the U.S. population takes benzodiazepine hypnotics (as compared to 2.4% in 1979), the number of individuals in the U.S. alone who develop tolerance to, and dependence upon, these drugs can be estimated at 560,000. These numbers do not include substance use outside medical or social norms and multiple drug abuse. No method of rapid withdrawal followed by an effective alternative treatment has yet been reported in patients who developed dependence on benzodiazepine hypnotics and this problem is a great obstacle in the rehabilitation and recovery of narcotic drug addicts.

It is well known that melatonin, an indole-derived hormone produced at night by the pineal gland, plays a major physiological role in the regulation of sleep. Melatonin is produced and secreted into the plasma in a circadian rhythm which parallels the sleep-wake cycle. A derangement of-the normal, diurnal melatonin production often results in sleep disorders. Melatonin binding sites have been characterized in membrane preparations from mammalian brains. Autoradiographic studies have revealed the existence of melatonin binding sites in the human biological clock.

A reciprocal relationship has been shown to exist between benzodiazepines and melatonin. There is evidence that melatonin affects benzodiazepine receptors. For example, melatonin augments GABA and benzodiazepine binding to brain membranes. In addition, pinealectomy results in a significant decrease, whereas melatonin injections restore, the benzodiazepine receptor density in the cerebral cortex of the rat. See, for example, Cardinali, D. P., et al. *Adv. Biochem. Psychopharm.* 42:155 (1986); Acun Castroviejo, D., et al. *J. Pineal Res.* 3:101 (1986); and Niles, L.P., et al. *J. Neural Transm.* 70:117. Melatonin also can enhance the anxiolytic effects of diazepam in mice (Guardiola-Lemaitre, B., et al. *Pharmacol. Biochem. Behav.* 41:405 [1992]).

On the other hand, there is evidence that benzodiazepines affect melatonin production. More specifically, benzodiazepines have been reported to suppress the nocturnal rise in plasma melatonin and to shift its day-night rhythmicity in several mammalian species. It has not yet been established whether these effects are indirect through the effect on the circadian clock or due to direct modulation of the pineal gland via benzodiazepine receptors localized on the pinealocytes. It is known that benzodiazepines can potentiate gamma amino butyric acid (GABA)-induced inhibition of melatonin synthesis and secretion (McIntyre, I. M., et al., *Biol. Psychiat.* 24:105 [1988]) and that nocturnal enhancement of plasma melatonin could be suppressed by benzodiazepines in humans, thus leading to distortion in the diurnal melatonin rhythm (Kabuto, M., et al. *Endocr. Japon.* 33:405 [1986]). Moreover, it has been observed that chronic treatment with oxazepam modified the diurnal variations in the density of melatonin receptors at night in the rat brain and that this effect was not observed in pinealectomized animals (Anis, Y., et al. *J. Neural Transm.* 89:155 [1992]).

SUMMARY OF THE INVENTION

It surprisingly has been found that administration of melatonin concurrently with benzodiazepine drugs can (1) wean a patient away from dependence on, tolerance of, or addiction to such drugs and (2) prevent the occurrence of such symptoms in patients who have been diagnosed as requiring a benzodiazepine drug but who have not yet become dependent on, tolerant of, or addicted to that drug.

Thus, one embodiment of the present invention comprises treating a patient suffering from a dependence on, tolerance of, or addiction to at least one benzodiazepine by administering melatonin to the patient on a daily basis in an amount sufficient to treat said dependence, tolerance or addiction.

Another embodiment of the invention comprises treating a patient who has been diagnosed as having a condition susceptible to alleviation by the administration of a benzodiazepine, while simultaneously preventing said patient from becoming dependent on, tolerant of, or addicted to the benzodiazepine, wherein said method comprises administering to the patient said benzodiazepine in an amount effective to alleviate the condition in combination with melatonin in an amount effective to prevent the patient from becoming dependent upon, tolerant of, or addicted to the benzodiazepine.

It has been found that persons who are dependent upon, tolerant of, or addicted to a benzodiazepine typically have developed an endogenous melatonin deficiency or distortion as determined by plasma melatonin level and profile. Accordingly, a further embodiment of the present invention is directed to a method of treating a patient who is suffering from an endogenous melatonin deficiency or distortion due to the prolonged administration of a benzodiazepine drug wherein said method comprises administering to the patient an amount of melatonin which is effective to correct or compensate for the deficiency or distortion. In a preferred embodiment, the melatonin can be administered so as to produce in the patient a plasma melatonin profile which substantially simulates a normal endogenous melatonin profile.

Another embodiment of the invention provides a method for treating a patient who has been clinically diagnosed as having a condition susceptible to alleviation by administration of a benzodiazepine drug and who is risk of developing a melatonin deficiency or distortion, which method comprises administering to the patient a benzodiazepine drug in combination with melatonin on a daily basis wherein the melatonin is administered so as to maintain the patient's plasma melatonin profile substantially similar to a normal endogenous melatonin plasma profile.

The invention further relates to a pharmaceutical controlled release formulation comprising melatonin in combination with at least one pharmaceutical carrier, diluent or coating, wherein, upon administration to a human, the formulation releases melatonin over time such that the person's melatonin plasma profile substantially simulates the melatonin plasma profile of a human having a normal endogenous melatonin profile.

DETAILED DESCRIPTION OF THE INVENTION

Figure 1:
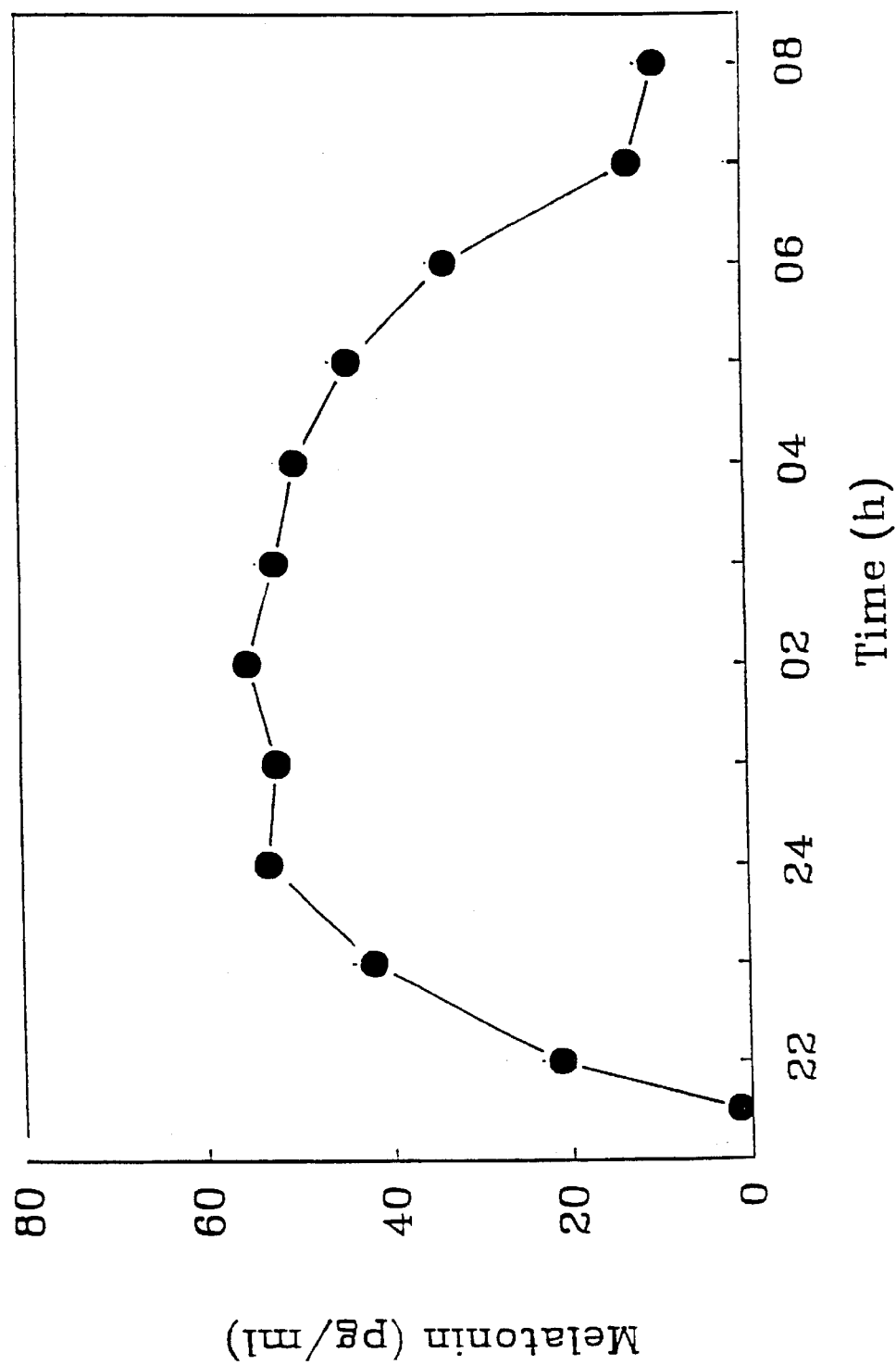
FIG. 1 illustrates the nocturnal plasma profile of melatonin concentration in a healthy adult human. This profile exemplifies the profile to be substantially simulated in accordance with a preferred embodiment of the present invention.

Applicant has found that persons who have become dependent upon, tolerant of, or addicted to benzodiazepines typically also suffer from an endogenous melatonin deficiency or distortion in comparison to a person with a normal endogenous plasma melatonin profile. A deficiency in endogenous melatonin production typically comprises the production of less than about 12 $\mu$g melatonin per night or less than 1.5 $\mu$g per hour during at least two hours during the night. A distortion of a person's endogenous melatonin profile occurs when peak melatonin production occurs during the daytime, prior to 2 hours after dusk or later than about 2 hours before dawn, or when daytime melatonin production is greater than a rate of 0.1 $\mu$g/hour, or a combination of the foregoing. Surprisingly, it has been found that administering melatonin to such a person in an amount sufficient to increase the amount of melatonin in the person's plasma at night to a substantially normal level for at least 4 hours of the night and, in one embodiment, to substantially simulate a normal melatonin night-time profile, can enable the person to overcome his or her dependence upon, tolerance of, or addiction to the benzodiazepine. Preferably, the melatonin is administered in an amount sufficient to increase the amount of melatonin in the person's plasma to normal levels.

By "substantially simulate" a normal profile is meant achieving minimal blood levels of about 60 to about 200 picograms melatonin per milliliter plasma, preferably about 100 to about 200 picograms melatonin per milliliter, and most preferably about 150 picograms melatonin per milliliter, for a period of at least 4 hours during the night. Maximal blood melatonin levels in a person with a normal melatonin profile typically are about 60 ±20 $\mu$g/ml, as shown in FIG. 1. The figure shows average melatonin levels throughout the body; it has been found that the melatonin level in those blood vessels which are close to the brain can be significantly higher than in peripheral veins. Accordingly, in order to affect the brain by exogenous melatonin, it is desirable to elevate the melatonin concentration in the blood to simulate the amounts present at night in the brain of a person with a normal endogenous melatonin profile. For an average size adult, this is approximately equivalent to the production of 4–7 $\mu$g/hour melatonin, typically about 5 $\mu$g/hour melatonin, during this period. The rise and decline of circulating melatonin should occur after sunset and before sunrise, respectively.

As noted above, a person can become tolerant of, dependent upon, or addicted to a benzodiazepine because he or she has been taking the benzodiazepine as a means of treating insomnia or to help overcome an addiction to other drugs, such as marijuana or heroin. Tolerance to a benzodiazepine results in having to administer an increasing amount of the drug due to a loss of effectiveness of the original dose. A person who is dependent upon a benzodiazepine is unable to sleep without the drug and suffers from rebound anxiety and restlessness when not given the drug. Symptoms of addiction include the symptoms of both dependence on and tolerance of the benzodiazepine and further can include headaches and impaired memory as a result of heavy sedation and the hypnotic effects of the benzodiazepine.

It has been found that these symptoms can be alleviated by administering on a daily basis a pharmaceutical formulation in oral, rectal, parenteral or transdermal form which comprises melatonin and at least one pharmaceutically acceptable diluent, carrier or adjuvant. Processes for making formulations for various methods of administration are well-known in the art. See, for example, Jones, B. E., "Hard Gelatin Capsules and the Pharmaceutical Formulator," *Pharm. Technol.* 9(9):106 (1985); Chandraskalan, S. K. et al. in *Sustained and Controlled Release Delivery Systems* (J. R. Robinson, ed.) Marcel Dekker, New York, 1978, p. 578; Lee, V. H. et al., Id. at pp 71–121; and Conine. J. W. et al., *Pharmaceutical Dosage Forms*: Tablets vol. 1 (H. A. Lieberman and L. Lachma, eds.) Marcel Dekker, New York, 1980, p. 267. Conveniently, the melatonin is administered in oral dosage form. Suitable carriers include lactose, calcium hydrogen phosphate and acrylic resin carriers such as those produced under the name Eudragit by Rohm Pharmaceuticals in Darstadt, Germany. Formulations suitable for oral administration can be prepared in the form of capsules or tablets. See, for example, Arendt et al., *British Medical Journal* 292:1170 (1986), which provides a description of melatonin in gelatin capsules.

Examples of benzodiazepines include, for example, alprazolam, chlordiazepoxide, chlorazepate, diazepam, fluorazepam, halazepam, lorazepam, oxazepam, prazepam, temazepam and triazolam.

The daily dosage of melatonin desirably is within the range of about 0.01 to about 100 mg, preferably within the range of about 0.5 to about 5 mg, and most preferably within the range of about 1 to about 2 mg for controlled release formulations and about 3 to about 5 mg for non-controlled release formulations. The higher amounts for non-controlled release formulations are desirable to compensate for the body's ability to metabolize melatonin quickly. The melatonin desirably is administered to the patient at night, just before bedtime. Preferably, the melatonin is administered between about 8:00 and about 11:00 p.m.

Melatonin analogs which substantially imitate the function of melatonin in the human body can be used in place of melatonin in the formulations and methods of the present invention. Such analogs are known to persons of skill in the art and include those listed in Depreux et al., *J. Med. Chem.* 37:3231–3239 (1994).

The melatonin can be administered, for example, once or twice daily at preselected times, in order to raise the level of melatonin in the person's blood to the desired level. In a preferred embodiment, the melatonin is administered so that the amount of melatonin in the person's blood will substantially simulate the normal plasma melatonin night time profile. Preferably, the formulation will be administered before sleep, so that the desired profile will be achieved while the patient sleeps.

If desired, the melatonin can be provided in a controlled release form. In a preferred embodiment, the melatonin is in particulate form comprising coated particles and controlled release is achieved by providing a variety of particle sizes and/or by the use of at least two different coating materials which dissolve at different rates and/or by varying the thickness of the coating material(s) such that particulate melatonin coated with different thicknesses of coating materials dissolve at different rates. The coating material can comprise one or more natural or synthetic polymers, such as calcium phosphate, lactose, cellulose, hydroxypropyl cellulose or ammonium methacrylate copolymers. Coated melatonin particles can be prepared in accordance with conventional coating procedures. See, for example, McGinty, J. W., *Drugs and the Pharmaceutical Sciences* 36:113 Dekker Verlag NY 1988.

If desired, the melatonin can be administered in combination with a substance which alters the phase position or shape of the person's melatonin plasma profile, such as a melatonin receptor modifier or a melatonin profile modifier. As melatonin is known to act at a specific time of day and be ineffective at other times of the day due to diurnal variations in melatonin receptors, it is important that melatonin and its receptors be present simultaneously. Melatonin receptor modifiers include short-acting benzodiazepines, such as oxazepam and triazolam; melatonin profile modifiers include benzodiazepines, such as alprazolam (McIntyre et al. *Chronobiology International* 10:205–213 [1993]), beta-blockers, such as propranolol (Brismar et al. *Acta Medica Scandinavia* 223:525 [1988]) and serotonin uptake inhibitors, such as desipramine (Franey et al., *British J. Med. Pharmacol.* 22:73 [1986]) and alpha antagonists, such as clonidine (Lewy et al., *J. Pharmaceutics and Pharmacology* 38:55 [1986]). The same benzodiazepine can be administered, in principle, to modify both the receptor and the modifier profiles. To act on the melatonin profile, it must be present in the body at the time that the pineal is synthesizing melatonin. To modify the receptor profile, it must be present when it can affect the person's biological clock.

If the melatonin is administered in combination with a benzodiazepine as a melatonin profile or receptor modifier, it is desirable to reduce the quantity of the benzodiazepine over the course of the melatonin administration. Desirably, the benzodiazepine is reduced steadily and may be eliminated if the patient does not suffer symptoms of benzodiazepine withdrawal. Of course, if the patient suffers from a condition that requires the ongoing administration of a benzodiazepine, such as for the relief of anxiety, the patient should continue to take the drug for that condition. Desirably, in such a situation, the patient will take the benzodiazepine during the day and the melatonin in the evening.

The melatonin receptor modifiers and the melatonin profile modifiers typically are administered simultaneously with, or shortly before, the melatonin administration. The modifiers also can be administered subsequent to the administration of the melatonin. For example, if there is endogenous synthesis of melatonin during the day and not at night, the nighttime deficiency can be corrected by administering the melatonin at night while the daytime production can be prevented by administering a profile modifier in the early morning. The modifier can simply be incorporated into the formulation containing the melatonin or the modifier can be prepared in a separate formulation comprising at least one diluent, carrier or adjuvant. As with the melatonin, the modifier conveniently is administered in oral dosage form.

The melatonin receptor modifier or melatonin profile modifier can be administered in a pharmacologically active amount. The dosage of any particular modifier depends upon its therapeutic potency, but generally is within the range of about 0.01 mg to about 100 mg. Preferred dosages can be readily determined by persons skilled in the art.

By administering a melatonin receptor and/or profile modifier, one can adjust the patient's biological clock so that maximal melatonin receptors are present just before darkness (and, therefore, just before the administration of the melatonin).

As noted above, the melatonin generally is provided in a daily dosage form of about 0.01 to about 100 mg. If the melatonin is to be administered in combination with a melatonin receptor modifier or profile modifier, the amount of the modifier generally can be reduced gradually over successive days of the melatonin administration. For instance, as noted above, melatonin profile modifiers are administered if the patient is endogenously producing melatonin at the wrong time of the day (i.e., during daytime). The profile modifier administered in combination with melatonin can be discontinued when the melatonin profile becomes stabilized (the melatonin will act to synchronize the patient's biological clock and the endogenous daytime melatonin production typically will disappear within about 1–3 weeks).

If the melatonin is administered in combination with a receptor modifier, it may be possible to reduce the amount of modifier administered on a daily basis, depending upon the patient's response to the therapy. As an example, a benzodiazepine that is administered to serve as a melatonin receptor modifier can be administered according to the following profile:

| days | unit dosage of benzodiazepines within the range |
|---|---|
| 1 | 0.01–100 mg |
| 2 | 0.05–50 mg |
| 3 | 0.033–33.3 mg |
| 4 | 0.025–25 mg |

As an alternative to, or in addition to, the use of a melatonin receptor modifier or melatonin profile modifier, the melatonin can be administered in combination with light therapy. Light can be used to adjust a person's biological clock, much as described above for the chemical melatonin profile modifiers discussed above. In addition, a person who has insufficient exposure to light may have internal desynchronization of his bodily rhythms, which may result in melatonin being produced during the daytime rather than at night. In such cases, treatment only with melatonin will not be fully satisfactory, as the patient also will have melatonin in his blood during the daytime. Light is known to suppress melatonin production by the pineal gland, so in these circumstances light can be used to help blunt melatonin production during the day. Exposure to light during the daytime can be continued until the person's biological clock stabilizes. Thus, in accordance with the present invention, it would be desirable to encourage exposure to light during the day and avoidance of light at night.

In one embodiment of the present invention, the benzodiazepine which has been prescribed, either for treatment of insomnia or as an aid to the withdrawal from addiction to other drugs, is continued to be administered to the patient, concurrently with the melatonin, at a daily dose substantially the same as that given prior to commencing the melatonin therapy. It has been found, however, that the administration of melatonin may result in the patient requiring less of the benzodiazepine to treat his or her medical condition than had been needed prior to the onset of melatonin administration. Accordingly, in an alternative embodiment, the benzodiazepine is administered to the patient, concurrently with the melatonin, at a progressively decreasing daily dose in comparison to that administered prior to beginning the melatonin therapy. In this embodiment, the progressively decreasing daily dose is administered until a minimum effective daily dose is determined or until the benzodiazepine administration is decreased to zero, depending upon the patient's response or reaction to the withdrawal of the benzodiazepine.

Melatonin also can be administered to persons who have been diagnosed as having a condition susceptible to treatment with a benzodiazepine, and thus are at risk of becoming tolerant of, dependent upon, or addicted to the drug, but have not yet become tolerant of, dependent upon, or addicted to the drug. In this embodiment of the invention, the benzodiazepine is administered in an amount effective to alleviate the diagnosed condition and melatonin is administered concurrently in an amount effective to prevent the patient from developing a melatonin deficiency or impairment. In some instances, by administering melatonin in combination with the benzodiazepine, the benzodiazepine can be administered in a dose which is less than that typically necessary to alleviate the condition for which it has been prescribed.

In all of these embodiments, the prescribed benzodiazepine can be administered throughout the day or in combination with the melatonin.

The following table provides the amounts of benzodiazepine drugs typically used to obtain sedative, hypnotic or anxiolytic effects in adults. Further information regarding half-life, forms of administration and suitable dosages for children can be found in Goodman & Gilman's *The Pharmaceutical Basis of Therapeutics,* 7th edition, 1985 (MacMillan Publishing Company). The passages relating to the use of benzodiazepines (e.g., pp. 352, 437) are incorporated herein by reference. Melatonin can be administered in combination with each of these benzodiazepines in accordance with the embodiments of the present invention as set forth above.

| Benzodiazepine | Content of unit oral dosage mg (x per day) | | Usual daily oral dose, mg* |
|---|---|---|---|
| | Sedative | Hypnotic | Anxiolytic |
| Alprazolam | | | 0.75–1.5 |
| Chlordiazepoxide | 10–100 (1–3) | 50–100 | 15–40 |
| Chlorazepate | 3.75–15 (2–4) | 15–30 | 30 |
| Diazepam | 5–10 (3–4) | 5–10 | 4–40 |
| Flurazepam | | 15–30 | |
| Halzepam | | | 60–160 |
| Lorazepam | | 2–4 | 2–6 |
| Oxazepam | 15–30 (3–4) | 15–30 | 30–60 |
| Prazepam | | | 20–40 |
| Temazepam | | 15–30 | |
| Triazolam | | 0.25–0.5 | |

*generally divided into 2–4 unit doses; for further information including parenteral dosage rates, see Goodman & Gilman, loc cit
**When the benzodiazepine is to be used to achieve a sedative or hypnotic effect, the amount given is mg per tablet and the number in parenthesis indicates the number of tablets per day. The anxiolytic doses are given as total amount per day.

The present invention is illustrated by the following examples, which are not intended to be limiting.

EXAMPLE 1

Preparation and release profile of controlled release formulations of melatonin

Melatonin tablets were prepared as follows:

Two sets of tablets were made by compressing in a 7 mm cylindrical punch at 2.5 tons each of the following dry mixtures of ingredients: for tablet designated SR-A: 2 mg/tablet melatonin (Biosynth Co., Switzerland), an acrylic resin carrier (Eudragit RS100) (Rohm Pharmaceuticals) and lactose such that the resultant tablets comprised 48.8% Eudragit RS100, 50% lactose and 1.2% melatonin; for tablet designated SR-B: 2 mg/tablet melatonin, an acrylic resin carrier (Eudragit RSPO) (Rohm Pharmaceuticals), lactose, calcium hydrogen phosphate, talc and magnesium stearate, such that the resultant tablets comprise 1.3% melatonin, 35.3% Eudragit RSPO, 16,7% lactose, 41.4% calcium hydrogen phosphate, 1.3% talc and 4% magnesium stearate.

Each of tablet formulations SR-A and SR-B is a sustained release formulation.

A conventional, non-sustained release formulation (tablet C) was prepared similarly to tablet formulation SR-B, with the exception that the Eudragit RSPO was replaced by lactose.

The potential release profile of the three types of tablets first was investigated by in vitro dissolution of melatonin therefrom in distilled water at 37° C. The results in table A below show the % of melatonin content (mean value of 6 tablets) dissolved in the stated period of time:

TABLE A

| Time (hours) | 1 | 2 | 4 | 6 | 8 | 10 |
|---|---|---|---|---|---|---|
| melatonin (%) released from: | | | | | | |
| SR-A | 12 | 29 | 62 | 84 | 90 | 100 |
| SR-B | 32 | 51 | 76 | 88 | 100 | |
| C | 93 | 96 | 100 | | | |

The in vivo profile of the SR-A tablets was investigated by oral administration twice to a healthy male (age 36) at 10:00 am, i.e., when circulating melatonin levels are undetectable. The amount of melatonin released in vivo was determined by radioimmunoassay of its major metabolite, 6-sulfoxymelatonin, in the urine. The amount of urinary 6-sulfoxymelatonin closely reflects the blood level of the hormone. The results in table B below show the melatonin determined as a % of the total melatonin administered (mean value of 2 tablets).

TABLE B

In vivo release of melatonin from SR-A

| Time (hours) | 1 | 2 | 4 | 6 | 8 | 10 |
|---|---|---|---|---|---|---|
| % release at intervals | 10.7 | 25.7 | 40.6 | 14.0 | 7.0 | 1.9 |
| cumulative release % | 10.7 | 36.4 | 77.0 | 91.0 | 98.0 | 99.9 |

It is noted that the release of melatonin in vitro, as illustrated in Table A, provides only an approximate indication of the in vivo release profile due to the known phenomenon of the active compound being absorbed by the tissues in the early stages of release.

The amount of melatonin in the sustained release formulations can be changed (e.g., to 0.5, 1 or 5 mg/tablet) without affecting the release pattern found for the tablets containing 2 mg/tablet melatonin.

In accordance with the present invention, one or more melatonin receptor modifiers or one or more melatonin profile modifiers can be incorporated into the above formulations in amounts which have been described herein.

EXAMPLE 2

The in vitro and in vivo studies showing a relationship between benzodiazepines and melatonin referenced in the background section of this application were in the context of an acute or short-term exposure to benzodiazepines. They did not relate to chronic administration of the drug and to the development of tolerance. To study the possible interactions between melatonin and benzodiazepines in this context the following animal model was studied.

Study Design 20 male rats, maintained on a daily 14 hour light/10 hour darkness schedule, were divided into 4 groups, each consisting of 5 members:

Group 1 (the control group): rats were injected daily with 200 µl saline intraperitoneally for 21 days and were allowed to drink tap water.

Group 2 (the valium group): rats were injected daily with 1 mg diazepam dissolved in 200 µl saline for 21 days. They also were provided with regular tap water.

Group 3 (the melatonin group): rats were injected daily with 200 µl saline intraperitoneally. Their only available drinking water contained 0.4% by weight melatonin.

Group 4 (the valium/melatonin group): rats were injected with 1 mg diazepam and allowed to drink only water containing 0.4% by weight melatonin.

Each group was allowed food and water ad libitum. After 21 days the treatment was stopped. The animals were decapitated between 6:00 and 7:00 p.m. the next day, their brains were rapidly removed and crude synaptosomal pellets were prepared, and melatonin receptors were assessed using 2-$^{125}$I-melatonin, as described by Laudon, M., and N. Zisapel, *FEBS Lett.* 197:9 (1986). Benzodiazepine receptors were assessed by measuring the binding of radioactive benzodiazepine receptor probes $^3$H-flunitrazepam ($^3$H-FNZ) and $^3$H-RO 15-1788 as described by Amiri, Z. et al. *Brain Res.* 553:155 (1991). Binding parameters were calculated from the equilibrium binding data. Maximal binding (Bmax) values represent the specific binding of 2-$^{125}$I-iodomelatonin, $^3$H-FNZ or $^3$H-RO 15-1788 at saturation and Kd values are the apparent dissociation constants. Binding parameters of the various groups were compared by analysis of variance followed by Student-Newman-Keul's test for multiple comparison. Differences were considered significant if P<0.05.

In the medulla-pons of the animals which had been treated with diazepam for 21 days (Group 2), iodinated melatonin binding was lower than in the control group. Analysis of the data indicated that the mean density of binding sites in this group was 35% lower than the control value, with no significant differences in the dissociation constant. As expected, no difference was observed between the binding of melatonin in the group receiving the melatonin only and the control group.

In the brains of the animals of group 4, the decrease in melatonin binding was prevented. Moreover, an actual increase in the mean density of binding sites was observed not only in comparison with the valium treated group (145% rise) but also in relation to the control group and to the melatonin-only group (58%). The apparent dissociation constant (Kd) also increased in group 4.

Benzodiazepine binding assays in the medulla-pons showed that administration of diazepam for 21 days did not alter the density or the apparent affinity of RO-1788 (when compared with the control group). On the other hand, treatment with either melatonin alone or a combination with diazepam significantly increased the maximal binding (Bmax) of the RO-15-1788 binding sites.

No significant differences were observed between the two latter groups. In other words, melatonin was able to augment benzodiazepine binding sites in the medulla-pons.

The effects of prolonged diazepam and melatonin administration on tritiated RO 15-1788 and tritiated flunitrazepam binding in the cerebral cortex of the rats also was studied. Unlike the medulla-pons, there was a 20% reduction in specific binding of the melatonin treated animals as compared with the control group. This was observed in both RO 15-1788 and flunitrazepam assays. Diazepam treatment did not significantly affect the binding sites but prevented the melatonin-mediated decrease.

The results obtained in the present study clearly demonstrate, for the first time, that prolonged diazepam administration causes suppression of melatonin binding sites in the medulla-pons of the rat and that this suppression can be abrogated by administration of melatonin. The melatonin binding sites in the medulla-pons previously have been characterized as "low affinity" sites. The low affinity melatonin binding sites in the medulla pons and hypothalamus have been shown to correlate functionally with the ability of melatonin to inhibit dopamine release in vitro. The densities of these sites exhibit diurnal variations. There are two possible mechanisms which contribute to the decrease in iodinated melatonin binding sites in the medulla pons after chronic diazepam administration:

The first mechanism is the decrease in nocturnal melatonin production, induced by the benzodiazepine. This is supported by a previous observation by Zisapel and Laudon that in aged rats suppression of melatonin production is accompanied by a decrease in the density of melatonin binding sites and that the density increases following treatment with exogenous melatonin.

Alternatively, it is possible that the benzodiazepines, by phase-shifting the sleep-wake cycle, also shift the maximal melatonin binding density to a different hour, which could not be determined in the present study, as all of the animals were sacrificed at the same hour.

In conclusion, a reciprocal effect has been shown on the binding sites of melatonin and diazepam following prolonged administration.

Melatonin receptors are necessary for its effects on sleep-wake cycle. The data imply that melatonin plays an important role in the pathogenesis of benzodiazepine tolerance. It appears that prolonged treatment with benzodiazepine hypnotics lose their effectiveness through the diminution of melatonin-responsive mechanisms and consequent physiological activity.

EXAMPLE 3

This example illustrates the action of melatonin in facilitating rapid withdrawal from benzodiazepine tolerance. A 43 year old female, married with two children, had been suffering from sleep onset insomnia for 10 years, accompanied by frequent and severe migraine attacks. A thorough neurological assessment was negative. Psychiatric or other organic problems also were ruled out.

The patient had been treated with benzodiazepines, tricyclic antidepressants and neuroleptic drugs, as well as biofeedback and relaxation methods with no apparent relief throughout the 10 year period. For the last year, she had been taking 4–8 mg Lorazepam every night, taking a 0.5 mg tablet every half hour or hour throughout the night. This led to difficulties when the patient arose in the morning; she would feel heavily sedated and had problems functioning at work, especially when under pressure. She began to feel that she was losing her memory and ability to concentrate.

A thorough psychological assessment made at the Sleep Laboratory of Tel Aviv University did not disclose any significant pathology. The quality of sleep was assessed by an actigraph tracing which automatically monitors the bedtime sleep-wake pattern through a small device attached to the hand. The tracing was recorded for three consecutive days and showed a deranged sleep pattern: reduced efficiency, long sleep latency and multiple waking episodes. Urine was collected every three hours for 36 hours and assayed for the diurnal secretion of plasma melatonin. Results showed that 6-sulfoxymelatonin excretion levels were lower than for age-matched individuals and lacked the typical circadian rhythm. See table C.

Oral administration of a controlled release melatonin formulation in the form of tablets containing 1 mg melatonin (Neurim Pharmaceuticals, Israel) (made in accordance with the procedures set forth in example 1 for tablet SR-A) was initiated in order to correct for the deficiency and distortion of the melatonin rhythm. One tablet was administered daily at 8:30 p.m. The patient was asked to gradually reduce the number of benzodiazepine tablets taken each night. Surprisingly, within 2 days, the patient stopped using the benzodiazepine hypnotics altogether and claimed that her insomnia had improved remarkably. In addition, the patient reported that her headaches also subsided gradually. A repeated actigraph tracing after 3 weeks of melatonin treatment showed marked improvement in her sleep pattern.

The treatment was stopped and 2 weeks afterwards the patient's urine was collected again every three hours over a 36 hour period and assayed for 6-sulfatoxymelatonin. The results, provided in the table below, indicated an increase in amount and a clear nocturnal peak of urinary 6-sulfatoxymelatonin. These results showed that the timing of the patient's melatonin rhythm was normal, although the amount of melatonin was still slightly less than normal. A three month follow-up confirmed that the patient maintained her quality of sleep and hardly suffered from headaches. After 6 months without treatment the patient's sleep quality began to deteriorate and melatonin therapy was resumed. The therapy restored her sleep quality and the patient continues to take 3 mg melatonin daily.

TABLE C

Urinary 6-sulfatoxymelatonin in benzodiazepine-dependent patient before and after melatonin therapy ($\mu$g/hour)

| Time | before treatment | after treatment |
|---|---|---|
| 15.00 | 0.3 | 0.11 |
| 18.00 | 0.16 | 0.45 |
| 21.00 | 0.18 | 0.11 |
| 24.00 | 0.13 | 1.24 |
| 3.00 | 0.23 | 0.74 |
| 6.00 | 0.23 | 0.36 |
| 9.00 | 0.22 | 0.21 |
| 12.00 | 0.13 | 0.01 |
| 15.00 | 0.22 | 0.04 |

EXAMPLE 4

This example illustrates the effects of long term administration of melatonin in the treatment of insomnia in patients dependent upon a benzodiazepine.

Two volunteers, Y. L., an 80 year old male, and E. L., a 73 year old female, had each suffered for a number of years from insomnia and/or frequent awakenings during the night accompanied by difficulty in falling asleep again. Both were found to have low melatonin secretion as determined by urine analysis and determination of the amount of the metabolite 6-sulphatoxymelatonin. Both patients had been taking 1–2 mg of flunitrazepam orally prior to retiring each evening.

Each patient was weaned off of the flunitrazepam via gradual reduction and simultaneous administration of melatonin over a two month period. During this time, each patient received 2 mg melatonin in controlled release form daily. Since the end of that two month period, each patient has been taking 2 mg oral controlled release melatonin for almost two years.

Each patient subjectively has reported good sleep inducement and a substantial improvement in sleep quality. Specifically, patient E. L. noted an improvement in sleep quality as of the beginning of the weaning period and Y. L. noted the same about two weeks into the weaning period. Each patient also reported reduced fatigue during the daytime within several days after the beginning of the weaning period. Each patient has indicated that the melatonin has not caused any residual tiredness in the morning nor any hangover feeling. No side effects have been reported by either patient.

What is claimed is:

1. A method of treating a patient who has been diagnosed as having a condition susceptible to alleviation by administration of a benzodiazepine, while simultaneously preventing said patient from becoming dependent on, tolerant of, or addicted to said benzodiazepine, which method comprises administering to said patient said benzodiazepine in an amount effective to alleviate said condition in combination with a controlled release form of melatonin, wherein the controlled release form of melatonin provides for the release of melatonin in the patient's body such that the patient maintains a substantially normal plasma melatonin profile, thereby preventing said patient from becoming dependent on, tolerant of, or addicted to said benzodiazepine.

2. A method in accordance with claim 1, wherein the melatonin is administered in an amount such that the patient achieves a minimal blood level of about 60 to about 200 picograms melatonin per milliliter over at least four hours following the administration.

3. A method in accordance with claim 2, wherein the melatonin is administered in an amount such that the patient achieves a minimal blood level of about 100 to about 150 picograms melatonin per milliliter over at least four hours following the melatonin administration.

4. A method in accordance with claim 1, wherein the melatonin is administered in a daily dosage within the range of about 0.5 mg to about 5 mg.

5. A method in accordance with claim 1, wherein the melatonin is administered in combination with a melatonin receptor modifier or a melatonin profile modifier.

6. A method in accordance with claim 5, wherein the melatonin receptor modifier comprises a short-acting benzodiazepine.

7. A method in accordance with claim 5, wherein the melatonin profile modifier comprises a benzodiazepine, a beta blocker or a serotonin uptake inhibitor.

8. A method in accordance with claim 1, where the melatonin is administered in conjunction with light therapy.

9. A method in accordance with claim 1, wherein the benzodiazepine drug is administered at a daily dosage level which is conventionally administered to alleviate said condition.

10. A method in accordance with claim 1, wherein the benzodiazepine drug is administered at a daily dose which is less than that which is conventionally administered to alleviate said condition.

11. A method in accordance with claim 6, wherein the melatonin receptor modifier is administered at a daily dosage level of about 0.01 to about 100 mg.

12. A method in accordance with claim 7, wherein the melatonin profile modifier is administered at a daily dose of about 0.01 to about 100 mg.

13. A method for preventing a melatonin deficiency or distortion in the plasma melatonin level and profile in a human, wherein the human is being administered a benzodiazepine drug to alleviate a condition susceptible to alleviation by administration of said benzodiazepine drug and wherein the human is at risk of becoming dependent upon, tolerant of, or addicted to said benzodiazepine, which comprises administering melatonin to said human on a daily basis, wherein said melatonin is administered in an amount effective to maintain a substantially normal plasma melatonin profile.

14. A method in accordance with claim 13, wherein the melatonin is administered in a controlled release form.

* * * * *